US006297361B1

(12) United States Patent
Haak-Frendscho et al.

(10) Patent No.: US 6,297,361 B1
(45) Date of Patent: Oct. 2, 2001

(54) USE OF HISTIDINE DECARBOXYLASE IMMUNOREACTIVITY TO DETECT HUMAN CANCER

(75) Inventors: Mary Haak-Frendscho, Madison, WI (US); Andras Falus, Erd (HU)

(73) Assignee: Promega Corporation, Madison, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/779,814

(22) Filed: Jan. 6, 1997

(51) Int. Cl.$^7$ .......................... C07K 16/40; C07K 16/18; G01N 33/53

(52) U.S. Cl. ..................... 530/387.7; 530/387.9; 530/388.1; 530/388.26; 530/388.8; 530/388.85; 530/389.1; 530/389.7; 530/387.1; 435/975; 436/64

(58) Field of Search .......................... 424/130.1, 155.1; 530/300, 387.1, 388.1, 387.7, 387.9, 388.26, 388.8, 388.85, 389.1, 389.7; 435/7.4, 7.1, 42.52, 975; 436/64

(56) References Cited

U.S. PATENT DOCUMENTS 4,550,019 * 10/1985 Polson .
4,636,463 * 1/1987 Altman et al. .

FOREIGN PATENT DOCUMENTS 8338841    12/1996 (JP) .
WO96/15249  5/1996 (WO) .

OTHER PUBLICATIONS

Köhler and Milstein, Nature 256:495, 1975.*
"Human Histidine Decarboxylase (HDC) mRNA, complete sequence", *GenBank*, Accession No: M60445 (Nov., 1994).
"Rat Histidine Decarboxylase (HDC) mRNA, complete sequence", *GenBank*, Accession No: M29591 (Jan., 1991).
G. P. Cricco, et al., "Histamine as an Autocrine Growth Factor in Experimental Mammary Carcinomas", *Agents and Actions*, 43, 17–20 (1994).
H. Fukui, et al., "Immunochemical Cross Reactivity of the Antibody Elicited Against L–Histidine Decarboxylase Purified from the Whole Bodies of Fetal Rats with the Enzyme From Rat Brain", *Biochem. Biophys. Res. Comm.*, 93, 333–339 (1980).
M. Garcia–Caballero, et al., "Changes in Histamine Synthesis, Tissue Content and Catabolism in Human Breast Cancer", *Agents and Actions*, 27, 227–231 (1989).

M. Garcia–Caballero, et al., "Increased Histidine Decarboxylase (HDC) Activity in Human Colorectal Cancer: Results of a Study on Ten Patients", *Agents and Actions*, 23, 357–360 (1988).

Y. Taguchi, et al., "Immunohistochemical Analysis of the Cross–Reaction of Anti–Rat Histidine DecarboxylaseAntibody with guinea–Pig DOPA Decarloxylase", *Brain Res.*, 340, 235–242 (1985).

T. Watanabe, et al., "Evidence for the Presence of a Histaminergic Neuron System in the Rat Brain: An Immunohistochemical Analysis", *Neuroscience Lett.*, 39, 249–254 (1983).

K. Yatsunami, et al., "Comparative Studies of Human Recombinant 74–and 54–kDa L–Histidine Decarboxylases", *J. Biol. Chem.*, 270, 30813–30817 (Dec., 1995).

Goueli, S.A., et al., "Polyclonal Antibodies Against Rat Liver Cytosolic Casein Kinase II (CK–2) Cross–React with CK–2 From Other Tissues and Nuclear Form (PK–N2) of the Enzyme", *Biochemistry International*, vol. 21, 685–694, (Aug. 1990).

Joseph, D.R., et al., "Characterization and expression of the complementary DNA encloding rat histidine decarboxylase", *Proc. Natl. Acad. Sci. USA*, vol. 8, pp. 733–737, (Jan. 1990).

Kondo, S., et al., "Determination of histidine decarboxylase mRNA in various rat tissues by the polymerase chain reaction", *Inflamm. Res.*, vol. 44, pp. 111–115, (1995).

Larsson, A., et al., "Chicken IgY: Utilizing the Evolutionary Difference", *Comparative Immunology, Microbiology and Infectious Diseases*, vol. 13, 199–201, (1990).

Pollard, H., et al., "Monoclonal Antibody Against 1–Histidine decarboxylase for Localization of Histaminergic Cells", *Neuroscience Letters*, vol. 54, pp. 53–58, (1985).

Yamauchi, K., et al., "Nucleotide Sequence of the cDNA encloding L–histidine decarboxylase derived from human basophilic leukemia cell line, KU–812–F", *Nucleic Acids Research*, vol. 18, No. 19, (1990), p. 5891.

* cited by examiner

*Primary Examiner*—Anthony C. Caputa
*Assistant Examiner*—Anne L. Holleran
(74) *Attorney, Agent, or Firm*—Schwegan, Lundberg, Woessner & Kluth

(57) ABSTRACT

The present invention provides a purified antibody which specifically reacts with human histidine decarboxylase (HDC), as well as immunogenic compositions comprising HDC peptides.

13 Claims, 6 Drawing Sheets

USE OF HISTIDINE DECARBOXYLASE IMMUNOREACTIVITY TO DETECT HUMAN CANCER

BACKGROUND OF THE INVENTION

Histamine has a pivotal role in a variety of in vivo reactions. Endogenous histamine plays an important role in regulating cell proliferation in normal and neoplastic cells. Increased histamine biosynthesis and content has been reported in different human and experimental neoplasias (Cricco et al., *Agents and Actions*, 43:17 (1994); Garcia-Caballero et al., *Agents and Actions*, 27:227 (1989); Scolnik et al., *Trends Pharmacol. Sci.*, 6:357 (1985)). Using histamine receptor antagonists, in vitro and in vivo experiments (Van der Ven et al., *Br. J. Cancer*, 68:475 (1990); Watson et al., *Gut*, 34:1091 (1993)) have demonstrated that histamine acts through the specific histamine membrane receptors, H1, H2 and H3, and may regulate tumor growth and development (Cricco et al., *Agents and Actions*, 38:175 (1993)). However, the most compelling evidence supporting a central role for histamine in neoplasia are the results of clinical trials showing increased survival of gastric cancer patients after treatment with cimetidine, an H2 receptor antagonist (Tonnesen et al., *Lancet*, ii:990 (1988); Burtin et al., *Eur. J. Cancer Clin. Oncol.*, 24:161 (1988)). In addition to promoting proliferation of tumor cells, histamine also has potent immunosuppressive effects which can favor tumor cell growth, for example by blunting NK activity (Hellstrand et al., *Scand. J. Immunol*, 34:741 (1991)) and by activating T-suppressor cell function (Bartholeyns et al., *Trends Pharmacol. Sci.*, 7:23 (1985)).

Histamine levels in cells and tissues are regulated by histidine decarboxylase (HDC), the only enzyme that catalyzes the formation of histamine from L-histidine. Thus, HDC is both a specific marker for histamine and an early indicator of histamine-mediated proliferation and immune suppression. Increased HDC activity has been measured in human colorectal tumor specimens (Garcia-Caballero et al., *Agents and Actions*, 23:357 (1988)). Moreover, the inhibitory effects of α-fluoromethyl-histidine, a suicide inhibitor of HDC (Watanabe et al., *Trends Pharmacol. Sci.*, 11:363 (1990)), have been demonstrated in tumor models (Bartholeyns et al., *Cancer Res.*, 44:639 (1984); Brandes et al., *Agents and Actions*, 33 (Suppl.):325 (1991)).

Although anfibodies to HDC have been developed, the first such antibody was a preparation of polyclonal antibodies of limited use due to its species specificity, i.e., the polyclonal antibodies proved useful only for rat studies (Watanabe et al., *Neurosci. Lett.*, 39:249 (1983); Taguchi et al., *Brain Res.*, 340:235 (1985)). Yatsunami and colleagues reported the generation of a HDC monoclonal antibody (mAb), using a peptide sequence conserved across human and rat HDC (*J. Biol Chem.*, 270:30813 (1995)). However, this antibody recognized only denatured HDC.

Thus, a need exists for antibodies to HDC which are useful to detect HDC in tissue specimens, e.g., antibodies which recognize native human HDC in tumor biopsies.

SUMMARY OF THE INVENTION

The present invention provides an isolated, purified antibody, or a preparation of antibodies, that specifically reacts with, or binds to, at least the native form of mammalian histidine decarboxylase (HDC), a biologically active subunit thereof, or a biologically active variant thereof. A preferred antibody of the invention is a preparation of polyclonal antibodies that specifically binds to the native form of human HDC. Preferably, the antibodies of the invention are substantially free of antibodies that do not react with HDC.

Peptides useful in preparing the antibodies of the invention preferably include a peptide comprising an amino acid sequence corresponding to EPEEYRERGREM (SEQ ID NO:1), VKDKYKLQ (SEQ ID NO:2), subunits or variants thereof. Thus, a preferred embodiment of the invention includes a preparation of polyclonal antibodies that specifically reacts with a protein or polypeptide which comprises a peptide having an amino acid sequence corresponding to SEQ ID NO:1, SEQ ID NO:2, a subunit or variant thereof. As described hereinbelow, polyclonal antibodies generated to HDC peptides can bind to, and label, melanoma and leukemia cells. Moreover, the polyclonal antibodies differentially stain different staged melanoma biopsies.

As used herein, the term "a variant" of a peptide of the invention is defined to mean a peptide which has at least about 70%, preferably at least about 80%, and more preferably at least about 90%, identity or homology to a peptide having SEQ ID NO:1 or SEQ ID NO:2.

As used herein, "biologically active" with respect to a subunit or variant of a HDC peptide of the invention means that the subunit or variant peptide has at least about 10%, preferably at least about 50%, and most preferably at least about 90%, the activity of a peptide having the amino acid sequence corresponding to SEQ ID NO:1 or SEQ ID NO:2. The activity of a peptide of the invention can be measured by methods well known to the art including, but not limited to, the ability of the peptide to elicit a sequence-specific immunologic response when the peptide is administered to an organism, e.g., chicken, goat, sheep or mice.

The invention also provides an expression cassette comprising a first preselected DNA segment encoding at least one immunogenic HDC peptide, e.g., a peptide comprising the amino acid sequence corresponding to SEQ ID NO:1, SEQ ID NO:2, a subunit or variant thereof, which is operably linked to a promoter functional in a host cell. The expression cassette preferably comprises a promoter functional in a prokaryotic cell. Preferably, the expression cassette further comprises a second DNA segment encoding a carrier protein, wherein the first and second preselected DNA segments are linked so as to encode a fusion peptide. The carrier protein provides T helper cell activation and, preferably, has low immunoreactivity. The expression cassettes can be incorporated into expression vectors which can be employed to transform prokaryotic or eukaryotic host cells, so as to result in expression of an immunogenic HDC peptide, preferably comprising the amino acid sequence corresponding to SEQ ID NO:1 or SEQ ID NO:2. As used herein, the term "immunogenic HDC peptide" means those regions of HDC which are capable of eliciting an immune response, wherein the resulting antibodies are capable of specifically reacting with mammalian HDC.

The invention also provides an immunogenic composition or a vaccine comprising a peptide which comprises the amino acid sequence corresponding to SEQ ID NO:1, SEQ ID NO:2, a biologically active variant or subunit thereof, preferably linked directly through a peptide bond to a carrier protein, in combination with a pharmaceutically acceptable carrier. The administration of the immunogenic composition or vaccine to a mammal induces the production of antibodies to HDC.

The invention further provides methods of detecting or determining the presence or amount of histidine decarboxylase RNA or polypeptide in a mammalian physiological sample which comprises cells (e.g., fluids comprising mammalian cells or tissue samples). One embodiment of the invention comprises a diagnostic method for detecting histidine decarboxylase RNA. The method comprises contacting an amount of DNA with an amount of at least two oligonucleotide primers under conditions effective to amplify the DNA by a polymerase chain reaction so as to yield an amount of amplified histidine decarboxylase DNA. The DNA is obtained by reverse transcription of RNA from a mammalian physiological sample which comprises cells suspected of containing histidine decarboxylase RNA. At least one oligonucleotide is a histidine decarboxylase-specific oligonucleotide. Then the presence or amount of the amplified histidine decarboxylase DNA is detected or determined.

As used herein, the term "histidine decarboxylase-specific oligonucleotide or primer" means a DNA sequence that has at least about 80%, more preferably at least about 90%, and more preferably at least about 95%, sequence identity or homology to a portion of the DNA encoding human histidine decarboxylase. An oligonucleotide or primer of the invention has at least about 7–50, preferably at least about 10–40, and more preferably at least about 15–35, nucleotides. Preferably, the oligonucleotide or primer of the invention comprises at least 7 nucleotides at the 3' of the oligonucleotide or primer which has at least about 80%, more preferably at least about 85%, and more preferably at least about 90%, identity to the DNA encoding human histidine decarboxylase. The oligonucleotide or primer of the invention may also include sequences which are unrelated to histidine decarboxylase nucleic acid sequences, e.g., they may encode restriction endonuclease recognition sequences. A preferred oligonucleotide or primer of the invention comprises SEQ ID NO:3. Another preferred oligonucleotide or primer of the invention comprises SEQ ID NO:4.

The invention also provides a method for detecting melanoma in a mammal having, or at risk of, melanoma. The method comprises contacting an amount of DNA from a sample to be tested with an amount of at least two oligonucleotides under conditions effective to amplify the DNA by a polymerase chain reaction so as to yield an amount of amplified histidine decarboxylase DNA product. The DNA product is obtained by reverse transcription of RNA from a mammalian physiological sample which comprises cells suspected of containing histidine decarboxylase RNA. At least one oligonucleotide is a histidine decarboxylase-specific oligonucleotide. The amount of the amplified histidine decarboxylase DNA product is then determined or detected and compared to the amount of amplified histidine decarboxylase in a control sample of mammalian physiological fluid which comprises cells. An amount of amplified histidine decarboxylase DNA product which is different than the amount of control amplified histidine decarboxylase DNA product is indicative of the presence of melanoma.

Further provided is a method for detecting a mammal having, or at risk of, melanoma. The method comprises contacting an amount of a labeled probe with a sample of mammalian physiological material which comprises mammalian cells, which cells are suspected of containing histidine decarboxylase mRNA, for a sufficient time to form binary complexes between at least a portion of said amount of probe and at least a portion of the RNA in the cells in the sample. The labeled probe comprises a preselected DNA segment complementary to a RNA molecule encoding mammalian histidine decarboxylase. The amount of binary complexes is then determined or detected relative to an amount of complexes formed in a control sample. The control sample is obtained by contacting a second amount of the labeled probe with a sample of mammalian cells which does not comprise melanoma cells for a sufficient time to form binary complexes between at least a portion of said amount of probe and at least a portion of the RNA in the cells in the sample. The amount of complexes formed in the sample suspected of containing histidine decarboxylase RNA which is different than the amount of control complexes is indicative of the presence of melanoma.

Also provided is a method for detecting or determining histidine decarboxylase in a mammalian physiological sample. The method comprises contacting an amount of purified antibodies which specifically react with histidine decarboxylase with the sample to be tested for a sufficient time to form binary complexes between at least a portion of the antibodies and a portion of the histidine decarboxylase in the sample. The antibodies preferably react with at least the native form of histidine decarboxylase. The presence or amount of said binary complexes is detected or determined, as by means of a second labeled antibody which binds to said complexes.

The invention further provides a diagnostic method for detecting cancer in a mammal at risk of, or afflicted with, cancer, such as melanoma or leukemia. The method comprises contacting an amount of purified antibodies which specifically react with histidine decarboxylase with a physiological sample obtained from the mammal for a sufficient time to form binary complexes between at least a portion of the antibodies and a portion of histidine decarboxylase. The amount of the binary complexes is then determined or detected, wherein the amount of said complexes is indicative of a mammal at risk of, or afflicted with, cancer. Preferably, the complex formation is detected by a second agent, such as an antibody comprising a detectable label or which binds to a detectable label, to form a detectable ternary complex. Preferably, the method detects the presence melanoma.

The invention also provides a diagnostic kit for detecting histidine decarboxylase in cells of a mammalian physiological sample which comprises packaging, containing, separately packaged, (a) a known amount of a first agent which binds to at least the native form of human histidine decarboxylase; and (b) a known amount of a second agent, which binds the first agent and does not bind to histidine decarboxylase, wherein the second agent is detectably labeled or binds to a detectable label.

The invention further provides a diagnostic kit for detecting melanoma. The kit comprises packaging, containing a known amount of a first agent which specifically binds to at least the native form of human histidine decarboxylase polypeptide. The kit also contains a known amount of a second agent, which binds to the first agent and does not bind to histidine decarboxylase, wherein the second agent is detectably labeled or binds to a detectable label.

DETAILED DESCRIPTION OF THE INVENTION

Figure 1A:
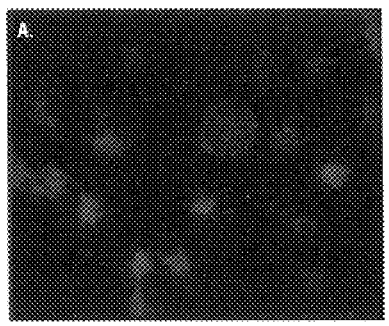
FIG. 1. Immunostaining of human basophilic leukemia and melanoma cell lines with anti-HDC antibodies. Human EP melanoma cells stained with HDC3-14 (A), HDC318-325 (B) or control IgY (C). CML basophilic leukemia cells stained with HDC3-14 (D) or HDC318-325 (E). Human WM-35 melanoma cells stained with HDC318-325 (F). Human HT-168 melanoma cells stained with HDC3-14 (G) or HDC318-325 (H). Human WM-983/B melanoma cells stained with HDC318-325 (I). Magnification 400×.
Figure 1B:
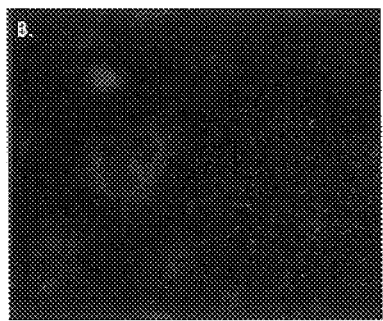

HPLC analysis showed that histamine levels were elevated in human melanoma and, in particular, that histamine levels were higher in primary melanoma lesions compared to metastatic melanoma lesions. Therefore, antibodies directed to L-histidine decarboxylase (HDC), the enzyme that catalyzes the synthesis of histamine, may have several clinical uses. For example, anti-HDC sera can be used as a reagent to detect rapidly proliferating mammalian cells such as cancer cells, e.g., melanoma or leukemia. Moreover, anti-HDC-antisera may be useful to immunostain mammalian biopsies to stage melanomas.

Peptides and Variants Useful to Prepare Antibodies. Candidate peptides having amino acids sequences which are unique to HDC and which have favorable antigenic characteristics are employed as immunogens. While other immunogenic HDC peptides may be useful to prepare antibodies capable of binding to HDC, it is preferred that a peptide comprising the amino acid sequence corresponding to SEQ ID NO:1, SEQ ID NO:2, a biologically active variant or subunit thereof, is employed in the practice of the invention.

Variant HDC peptides have at least one amino acid substitution relative to an amino acid sequence which comprises SEQ ID NO:1 or SEQ ID NO:2. In particular, amino acids are substituted in a relatively conservative manner. For example, hydrophobic residues are substituted for hydrophobic residues (norleucine, met, ala, val, leu, ile) neutral hydrophilic residues for neutral hydrophilic residues (cys, ser, thr), acidic residues for acidic residues (asp, glu), basic residues for basic residues (asn, gln, his, lys, arg), and aromatic residues for aromatic residues (trp, tyr, phe). However, the invention also envisions HDC variants with non-conservative substitutions. Non-conservative substitutions entail exchanging a member of one of the classes described above for another. After the substitutions are introduced, the variant peptides are screened for biological activity, e.g., ability to generate HDC antibodies or to specifically react with HDC-specific antibodies. To substitute a preselected amino acid residue for another amino acid residue, at least one nucleotide base in the codon encoding the amino acid is substituted with a different nucleotide base so as to encode the preselected amino acid residue. Methods to substitute one nucleotide base to another are well known to the art.

Preparation of HDC Peptides. Antibodies to HDC may be prepared using recombinant techniques to generate fusion peptide immunogens. For example, an expression cassette comprising an isolated DNA molecule, which encodes a fusion polypeptide or fusion peptide, operably linked to a promoter may be employed to prepare an immunogen. The isolated DNA molecule comprises a first preselected DNA segment encoding an immunogenic HDC peptide and, preferably, a second preselected DNA segment encoding a carrier protein. The carrier protein facilitates purification of the resulting fusion peptide and activates T helper cells. The carrier protein preferably possesses low immunoreactivity.

Generally, the expression cassette is in the form of chimeric DNA, and comprises plasmid DNA that can also contain coding regions flanked by control sequences which promote the expression of the preselected DNA segment once the expression cassette is introduced into host cell. Aside from preselected DNA sequences that serve as transcription units for HDC peptides, a portion of the DNA molecule may be untranscribed, serving a regulatory or a structural function.

Other elements functional in the host cells, such as introns, enhancers, polyadenylation sequences and the like, may also be a part of the DNA. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

"Control sequences" is defined to mean DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

"Operably linked" is defined to mean that the nucleic acids are placed in a functional relationship with another nucleic acid sequence. For example, DNA for a presequence or secretory leader can be operably linked to DNA coding for a polypeptide, and expressed as a prepolypeptide that participates in the secretion of the polypeptide; a promoter or enhancer can be operably linked to a coding sequence and affect the transcription of the sequence; or a ribosome binding site can be operably linked to a coding sequence and positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used to provide them in accord with conventional practice.

The expression cassette to be introduced into the cells further will generally contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA, dapA and the like. See also, the genes listed on Table 1 of Lundquist et al. (U.S. Pat. No. 5,848,956).

Reporter genes are used for identifying transformed cells and for evaluating the functionality of regulatory sequences. Reporter genes which encode for easily assayable polypeptides are well known in the art. In general, a reporter gene is a gene which is not present in or expressed by the recipient organism or tissue and which encodes a polypeptide whose expression is manifested by some easily detectable property, e.g., enzymatic activity. Preferred genes include the chloramphenicol acetyl transferase gene (cat) from Tn9 of *E. coli*, the beta-glucuronidase gene (gus) of the uidA locus of *E. coli*, and the luciferase gene from firefly *Photinus pyralis*. Expression of the reporter gene is assayed at a suitable time after the DNA has been introduced into the recipient cells.

The general methods for constructing recombinant DNA which can transform target cells are well known to those skilled in the art, and the same compositions and methods of construction may be utilized to produce the DNA useful herein. For example, J. Sambrook et al., *Molecular Cloning: A Laboratory Manual*, Cold Spring Harbor Laboratory Press (2d ed., 1989), provides suitable methods of construction.

A preferred expression cassette of the invention is an expression cassette which is operably linked to a promoter functional in a bacterial or insect cell. A preferred promoter useful in the practice of the invention is the T7 promoter.

The recombinant DNA can be readily introduced into host cells, e.g., mammalian, bacterial, yeast or insect cells by transfection with an expression cassette by any procedure useful for the introduction into a particular cell, e.g., calcium phosphate precipitation, lipofection, microinjection, electroporation, and the like, to yield a transformed cell, so that the preselected DNA segment of the present invention is expressed by the host cell.

The general methods for isolating and purifying a recombinantly expressed polypeptide or protein from a host cell are well known to those in the art. For example, the culture medium or lysate can be centrifuged to remove particulate cell debris. The insoluble and soluble polypeptide fractions are then separated. The fusion polypeptide of the invention may then be purified from the insoluble fraction, i.e., refractile bodies (see, for example, U.S. Pat. No. 4,518,526, the disclosure of which is incorporated by reference herein). Examples of the isolation and purification of recombinant polypeptides and proteins are given in Sambrook et al., cited supra.

Alternatively, the immunogenic HDC peptides can be synthesized by the solid phase peptide synthetic method (Stewart et al., *Solid Phase Peptide Synthesis*, W. H. Freeman Co., San Francisco (1969); Merrifield, *J. Am. Chem. Soc.*, 85 2149 (1963); Meienhofer in "Hormonal Proteins and Peptides," ed.; C. H. Li, Vol. 2 (Academic Press, 1973), pp. 48–267; and Bavaay and Merrifield, "The Peptides," eds. E. Gross and F. Meienhofer, Vol. 2 (Academic Press, 1980) pp. 3–285).

Preparation of Antibodies. The antibodies of the invention are prepared by using standard techniques, preferably, techniques for preparing polyclonal antibodies. To prepare polyclonal antibodies or "antisera," an animal is inoculated with an antigen, i.e., a purified immunogenic HDC peptide, and immunoglobulins are recovered from a fluid, such as blood serum, that contains the immunoglobulins, after the animal has had an immune response. For inoculation, the antigen is preferably bound to a carrier peptide and emulsified using a biologically suitable emulsifying agent, such as Freund's incomplete adjuvant.

Although a variety of mammalian or avian host organisms may be used to prepare polyclonal antibodies against HDC, chickens are a preferred host organism. Because it can be difficult to raise antibodies in a mammal to a mammalian polypeptide that is highly conserved between mammals, chickens, which are phylogenetically distant from mammals, can be useful immunologic hosts to prepare anti-sera to mammalian polypeptides (Brandes et al., *Biochem. Pharmacol.*, 40:1677 (1990); Carroll et al., *J. Biol Chem.*, 258:24 (1983); Gassman et al., *FASEB. J.*, 4:2528 (1990); Larson et al., *Comp. Immunol. Microbiol. Infect. Dis.*, 13:199 (1990); Asoka et al., *Immunol. Lett.*, 32:91 (1992)).

Moreover, avian IgG, also known as IgY (Leslie et al., *J. Exp. Med.*, 130:1337–1352 (1969)), is deposited in large quantities into the egg yolk and can be easily purified by sequential precipitation (Jensenius et al., *J. Immunol. Methods*, 46:63 (1981); Akita et al., *J. Food Science*, 57:629 (1992)). Furthermore, IgY is does not react with protein A (Langone et al., *J. Immunol. Methods*, 63:145 (1983); Katz et al., *J. Virol. Methods*, 12:59 (1985)), protein G (Guss et al., *EMBO J.*, 5:1567 (1986)), rheumatoid factor (Larsson et al., *J. Immunol. Methods*, 108:205 (1988)) and other human Ig (Larsson et al., *Hybridoma*, 11:33 (1992)) and does not activate the human complement system (Larsson et al., *J. Immunol. Methods*, 156:79 (1992)), all of which reduce the problem of non-specific reactivity. Thus, the use of IgY may provide advantages in some immunologic assays.

Following immunization, Ig is purified from the immunized bird or mammal. For certain applications, particularly certain pharmaceutical applications, it is preferable to obtain a composition in which the antibodies are essentially free of antibodies that do not react with the HDC peptide. This composition is composed virtually entirely of the high titer, monospecific, purified polyclonal antibodies to HDC peptides. Alternatively, antibodies are purified by affinity chromatography, using purified HDC peptide bound to a chromatographic support. Purification of antibodies by affinity chromatography is generally known to those skilled in the art (see, for example, U.S. Pat. No. 4,533,630). Briefly, the purified antibody is contacted with the purified HDC peptide bound to a solid support for a sufficient time and under appropriate conditions for the antibody to bind to the HDC peptide. Such time and conditions are readily determinable by those skilled in the art. The unbound, unreacted antibody is then removed, such as by washing. The bound antibody is then recovered from the HDC peptide by eluting the antibodies, by methods well known to the art, so as to yield purified, monospecific polyclonal antibodies.

Monoclonal antibodies against the HDC peptide can be also prepared, using known hybridoma cell culture techniques. In general, this method involves preparing an antibody-producing fused cell line, e.g., of primary spleen cells fused with a compatible continuous line of myeloma cells, and growing the fused cells either in mass culture or in an animal species, such as a murine species, from which the myeloma cell line used was derived or is compatible. Such antibodies offer many advantages in comparison to those produced by inoculation of animals, as they are highly specific and sensitive and relatively "pure" immunochemically. Immunol.ogically active fragments of the present antibodies are also within the scope of the present invention, e.g., the F(ab) fragment, as are partially humanized monoclonal antibodies.

It will be understood by those skilled in the art that the hybridomas herein referred to may be subject to genetic mutation or other changes while still retaining the ability to produce monoclonal antibody of the same desired specificity. The present invention encompasses mutants, other derivatives and descendants of the hybridomas.

It will be further understood by those skilled in the art that a monoclonal antibody may be subjected to the techniques of recombinant DNA technology to produce other derivative antibodies, humanized or chimeric molecules or antibody fragments which retain the specificity of the original monoclonal antibody. Such techniques may involve combining DNA encoding the immunoglobulin variable region, or the complementarity determining regions (CDRs), of the monoclonal antibody with DNA coding the constant regions, or constant regions plus framework regions, of a different immunoglobulin, for example, to convert a mouse-derived monoclonal antibody into one having largely human immunoglobulin characteristics (see EP 184187A, 2188638A, herein incorporated by reference).

Uses of Anti-HDC Antibodies. The antibodies of the invention are useful for detecting or determining the presence or amount of HDC polypeptide in a physiological sample, e.g., a mammalian tissue biopsy or a mammalian physiological fluid comprising cells, suspected of containing HDC polypeptide. The antibodies are contacted with the sample for a period of time and under conditions sufficient for antibodies to bind to the HDC polypeptide so as to form a binary complex between at least a portion of said antibodies and said HDC polypeptide. Such times, conditions and reaction media can be readily determined by persons skilled in the art.

For example, the physiological sample which comprises cells may be obtained from a mammal, e.g., a human. The cells are lysed to yield an extract which comprises cellular proteins. Alternatively, intact cells, e.g., a tissue sample such as paraffin embedded and/or frozen sections of biopsies, are permeabilized in a manner which permits macromolecules, i.e., antibodies, to enter the cell. The anti-HDC antibodies are then incubated with the protein extract, e.g., in a Western blot, or permeabilized cells, e.g., prior to flow cytometry, so as to form a complex. The presence or amount of the complex is then determined or detected.

The antibodies of the invention may also be coupled to an insoluble or soluble substrate. Soluble substrates include proteins such as bovine serum albumin. Preferably, the antibodies are bound to an insoluble substrate, i.e., a solid support. The antibodies are bound to the support in an amount and manner that allows the anti-HDC antibodies to bind HDC polypeptide (ligand). The amount of the antibodies used relative to a given substrate depends upon the particular antibody being used, the particular substrate, and the binding efficiency of the antibody to the ligand. The antibodies may be bound to the substrate in any suitable manner. Covalent, noncovalent, or ionic binding may be used. Covalent bonding can be accomplished by attaching the antibodies to reactive groups on the substrate directly or through a linking moiety.

The solid support may be any insoluble material to which the antibodies can be bound and which may be conveniently used in the assay of the invention. Such solid supports include permeable and semipermeable membranes, glass beads, plastic beads, latex beads, plastic microtiter wells or tubes, agarose or dextran particles, sepharose, and diatomaceous earth. Alternatively, the antibodies may be bound to any porous or liquid permeable material, such as a fibrous (paper, felt etc.) strip or sheet, or a screen or net. A binder may be used as long as it does not interfere with the ability of the antibodies to bind the ligands.

The invention also comprises reagents and kits for detecting the presence or amount of HDC in a sample. Preferably, the reagent or kit comprises the purified antibodies of the invention in a liquid that does not adversely affect the activity of the antibodies in the intended assay. Preferably, the liquid is saline solution. Alternatively, the reagent or kit may comprise the purified antibodies attached to a substrate as discussed above. Preferably, the substrate is an insoluble solid support, e.g., the well of a microtiter plate. An alternative preferred substrate is solid particles, most preferably latex beads.

The diagnostic kit comprises, in a container or packaging, one or more of the reagents of the invention and a means for detecting or measuring the formation of complexes created by the binding of HDC polypeptide and the antibodies in the reagents. The detecting or measuring means is preferably an immunoassay, such radioimmunoassay, enzyme-linked immunosorbent assay (ELISA), or an immunofluorescence assay. Most preferably, the detecting or measuring means is a reagent capable of binding to the complexes formed by the HDC and the antibodies and containing a detectable moiety. Such reagent may be the antibody of the invention conjugated with a detectable moiety. Alternatively, the antibody can be a second antibody, which is an antibody which binds to the antibodies of the invention, conjugated to a detectable moiety. An example of such a second antibody is rabbit anti-IgY-FITC conjugate.

Detection of HDC-Specific Transcripts by Reverse Transcriptase-Polymerase Chain Reaction (RT-PCR). To detect HDC encoding RNA transcripts, RNA is isolated from a cellular sample suspected of containing HDC RNA, e.g., total RNA isolated from a human melanoma cell line. RNA can be isolated by methods known to the art, e.g., using TRIZOL™ reagent (GIBCO-BRL/Life Technologies, Gaithersburg, Md.). In general, the isolated RNA is combined with a primer in a reverse transcriptase (RT) reaction to generate single strand cDNAs. Oligo-dT or random sequence oligonucleotides, as well as sequence specific oligonucleotides, can be employed as primers in the RT reaction. See Sambrook et al., supra. Resultant first-strand cDNAs are then amplified in PCR reactions.

"Polymerase chain reaction" or "PCR" refers to a procedure or technique in which amounts of a preselected fragment of nucleic acid, RNA and/or DNA, are amplified as described in U.S. Pat. No. 4,683,195. Generally, sequence information from the ends of the region of interest or beyond is employed to design oligonucleotide primers. These primers will be identical or similar in sequence to opposite strands of the template to be amplified. PCR can be used to amplify specific RNA sequences, specific DNA sequences from total genomic DNA, and cDNA transcribed from total cellular RNA, bacteriophage or plasmid sequences, and the like. See generally Mullis et al., *Cold Spring Harbor Symp. Quant. Biol.*, 51, 263 (1987); Erlich, ed., *PCR Technology*, (Stockton Press, NY, 1989). Thus, amplification of specific nucleic acid sequences by PCR relies upon oligonucleotides or "primers" having conserved nucleotide sequences. For example, one primer is prepared which is predicted to anneal to the antisense strand, and another primer prepared which is predicted to anneal to the sense strand, of a DNA molecule which encodes a HDC polypeptide.

To detect the PCR amplified product, the reaction mixture is typically subjected to agarose gel electrophoresis or another convenient separation technique, and the presence or absence of the HDC-specific amplified DNA is detected. Detection of the amplified HDC DNA may be accomplished by excising or eluting the fragment from the gel (for example, see Lawn et al., *Nucleic Acids Res.*, 9, 6103 (1981), and Goeddel et al., *Nucleic Acids Res.*, 8, 4057 (1980)), cloning the amplified product into a cloning site of a suitable vector and sequencing the cloned insert and comparing the DNA sequence to the known sequence of HDC. Alternatively, the HDC amplified DNA may be detected using Southern hybridization with an HDC-specific oligonucleotide probe, or comparing its electrophoretic mobility with DNA standards of known molecular weight.

The invention will be further described by the following examples.

EXAMPLE I

Antibody Development

Antibodies to HDC were prepared using recombinant methods to generate fusion peptide immunogens. Two peptides, corresponding to amino acid residues 3–14 (EPEEYRERGREM) (SEQ ID NO:1) and 318–325 (VKDKYKLQ) (SEQ ID NO:2) of the full-length human HDC polypeptide (SEQ ID NO:5; Yamauchi et al., *Nucl. Acids Res.*, 18, 5891 (1990); Zahnow et al., *DNA Seq.*, 1, 395 (1991)), were selected based on hydrophilicity (Hopp-Woods Hydrophilicity Plot), surface probability (Emini Surface Probability Plot), antigenicity (Jameson-Wolf Antigenic Index) and uniqueness when compared to other known proteins in the Gen Bank™ database. The corresponding oligonucleotides were inserted into a vector coding for a preselected carrier segment under the control of the T7 promoter (Knuth et al., WO 96/15249, the disclosure of which is incorporated by reference herein). The preselected carrier segment was designed by mutating all charged residues in the first 85 amino acid residues of the gene 10 protein of phage T7, including cys and met (except the initiator methionine), to hydrophobic residues. This carrier segment was designed to facilitate purification of the resulting fusion peptide and to augment T helper cell activation. The carrier segment was also designed to have low immunoreactivity. The low immunoreactivity results in the majority of the specific immune response being directed against the HDC peptide rather than the carrier segment.

*E. coli* transfected with the vector encoding the HDC-carrier protein fusion peptide were induced. Fusion peptides, expressed as inclusion bodies, were then purified by sequential detergent washes. The sparingly soluble fusion peptides were suspended in pyrogen free saline, admixed with equal volumes of Freund's adjuvant and used to immunize white leghorn hens.

Eggs were collected from the immunized hens beginning on day 35, following four subcutaneous 0.5 ml injections of 0.2 mg fusion peptide on days 0, 14, 21 and 28 of the immunization schedule. Total IgY was purified from the egg yolks of immunized hens by sequential precipitation using the EGGstract™ IgY Purification System per the manufacturer's instructions (Promega Corp., Madison, Wis.). The polyclonal antibodies to HDC amino acid residues 3–14 are termed HDC3-14 pAb while the polyclonal antibodies to HDC amino acid residues 318–325 are termed HDC318-325 pAb.

EXAMPLE II
Expression of HDC

To evaluate whether the anti-human HDC peptide antibodies could recognize HDC, Western blot analysis was performed. Extracts of the WM-983/B, EP and M1 human melanoma cell lines, human primary melanoma and skin tissues, and the fusion polypeptide, were subjected to SDS-PAGE then transferred onto nitrocellulose membranes. Each gel lane was loaded with 10 µg total extract protein. The transfers were blocked with PBS containing 0.05% (v/v) Tween-20 and 0.1% (w/v) BSA, probed with 50 µg/ml of HDC318-325 pAb, washed, incubated with 0.5 µg/ml HRP conjugate and developed with ECL reagent (Amersham Life Science, Buckinghamshire, UK). The results showed that lysates from three primary melanoma tissues, skin, EP, WM-983/B and M1 had a predominant band at 54 kDa, which corresponds to the reported size of the monomer form of human HDC. The band was absent in unstimulated human peripheral blood lymphocyte lysates.

To confirm that the polypeptide detected by Western blot was HDC, RNA was isolated from WM-35, WM-983/B, EP, HT-168 and M1 melanoma cell lines and analyzed for HDC RNA by RT-PCR. Cytoplasmic total RNA was isolated by the method described in Chomezinski and Sacchi (*Anal. Biochem.*, 162: 156 (1987)). HDC primers, designed to span exons ten and twelve, 5'-AATCTTCAAGCACATGTC-3' (SEQ ID NO:3) and 5'-CTGGATAGTGGCCGGGATGA-3' (SEQ ID NO:4) were employed in a RT-PCR. The pTN-2 plasmid containing the full length 2.4 kb cDNA encoding HDC was used as a positive control in the PCR. Actin primers were used as a control. PCR products were separated by agarose gel electrophoresis and visualized by ethidium bromide staining. The identity of the amplified product was confirmed by sequencing. The predicted 208 bp product was observed in all melanoma cells.

In situ hybridization was performed on WM-35 and WM-983/B melanoma cells. Cells were cultured on glass slides and then fixed in 4% (v/v) paraformaldehyde in PBS (pH 7.4). The denaturation-hybridization was performed in a Hybaid thermal cycler (Naoumov et al., *J. Clin. Pathol.*, 41:793 (1988)) using a biotinylated HDC probe (SEQ ID NO:3). Hybrids were detected using the ABC-AP method (Vector Laboratories, Burlingame, Calif.). Control cultures were processed in parallel without probe. Both WM-35 and WM-983/B cells showed HDC RNA by in situ hybridization analyses.

The WM-35 and WM-983/B human melanoma cell lines were also employed for flow cytometric analysis of HDC expression in cells. Cells, maintained in RPMI 1640 supplemented with 10% FBS, were washed in PBS containing 0.1% BSA and aliquoted at $5 \times 10^6$ cell/ml. The cells were then fixed in 1% (v/v) paraformaldehyde and permeabilized using 1% (v/v) Triton x-100®. The cells were subsequently stained for 30 minutes at 4° C. with 180 µg/ml HDC3-14 or 18 µg/ml HDC318-325 antibodies. Preimmune chicken antisera was used as a control. Following two PBS washes, cells were incubated for 30 minutes with 1 µg/ml FITC-conjugated secondary antibody. Cells then were washed with PBS and resuspended in 0.5 ml 1% paraformaldehyde. Propidium iodide was added immediately before flow cytometric analysis to gate out the dead cells. Fluorescence was examined on an Elite™ flow cytometer (Coulter, Hialeah, Fla.) using Elite 4.1 software.

Both HDC3-14 and HDC318-325 pAbs stained WM-35 and WM-983/B melanoma cells. The staining was dose-dependent. These findings demonstrate that the antibodies detect cellular HDC.

EXAMPLE III
HDC Immunostaining in Tumor Cell Lines, and in Primary and Metastatic Human Melanoma Tissues Because increased levels of histamine are associated with tumor cells, HDC may be an early indicator of neoplasia. To determine whether HDC3-14 and HDC318-325 pAbs could be employed for immunostaining, the antibodies were incubated with melanoma cell lines WM-35, WM-983/B, HT-168 and EP, the basophilic leukemia cell line CML, which is known to contain high levels of histamine, and human primary and metastatic melanoma tissues. Cells were grown on slides and fixed in MeOH for 10 minutes at −20° C. followed by a cold acetone rinse. Slides then were blocked with 0.5% BSA for 30 minutes. The primary antibodies were applied to the slides at 30 or 90 µg/ml HDC3-14 or 18 µg/ml HDC318-325 in PBS and incubated in a humidified chamber for 1 hour at room temperature. Control chicken IgY at an equivalent concentration was used to assess non-specific background staining. Following three PBS washes, the slides were incubated for 1 hour at room temperature with 0.5 µg/ml rabbit anti-chicken IgY FITC conjugate.

Figure 1C:
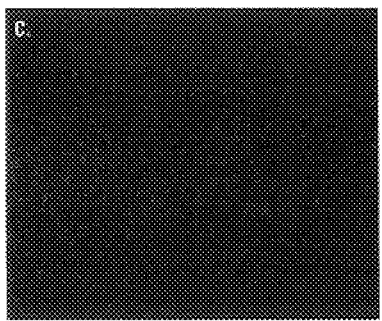
Figure 1D:
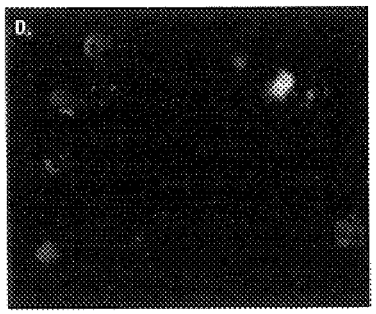
Figure 1E:
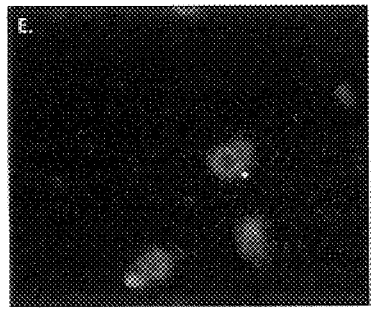
Figure 1F:
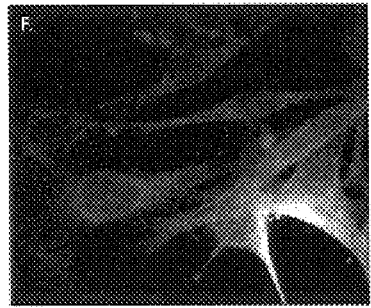
Figure 1G:
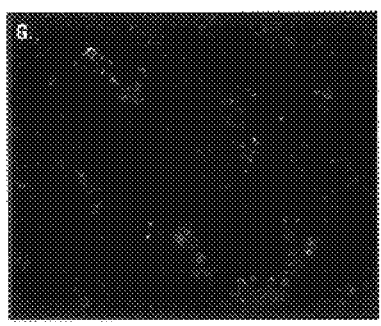
Figure 1H:
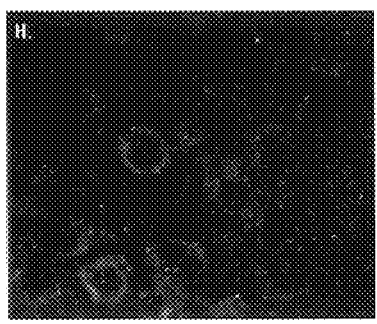
Figure 1I:
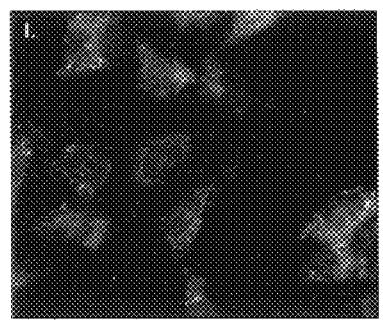

Strong punctate cytoplasmic staining was observed when CML basophilic leukemia cells were stained with HDC3-14 or HDC318-325 pAb (FIGS. 1D and E, respectively).

Similarly, human melanoma cells showed a bright, punctate cytoplasmic staining pattern when stained with HDC3-14 or HDC318-325 pAb, confirming that human melanoma cells contain abundant amounts of HDC (FIGS. 1A, B and F–I). Cells stained with control IgY showed minimal immunoreactivity (FIG. 1C).

Figure 2A:
FIG. 2. Immunostaining of human primary and metastatic melanoma tissue. Frozen sections from primary melanoma tissue stained with HDC3-14 (A) or HDC318-325 (B). Frozen sections from a subcutaneous metastatic lesion were stained with HDC3-14 (C), HDC318-325 (D) or control IgY (E). Magnification 400×(A and C–E), 100×(B).
Figure 2B:
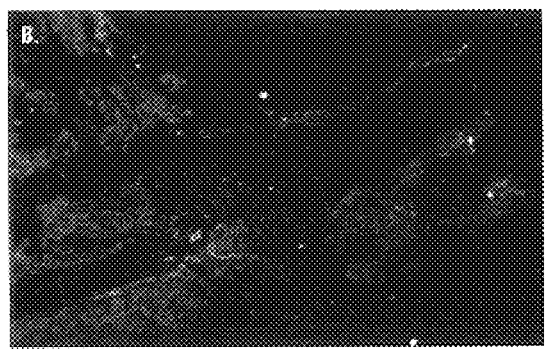
Figure 2C:
Figure 2D:
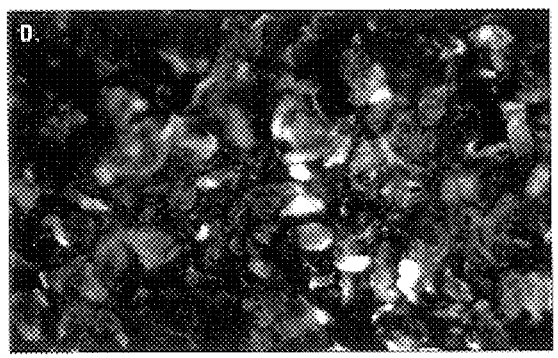
Figure 2E:
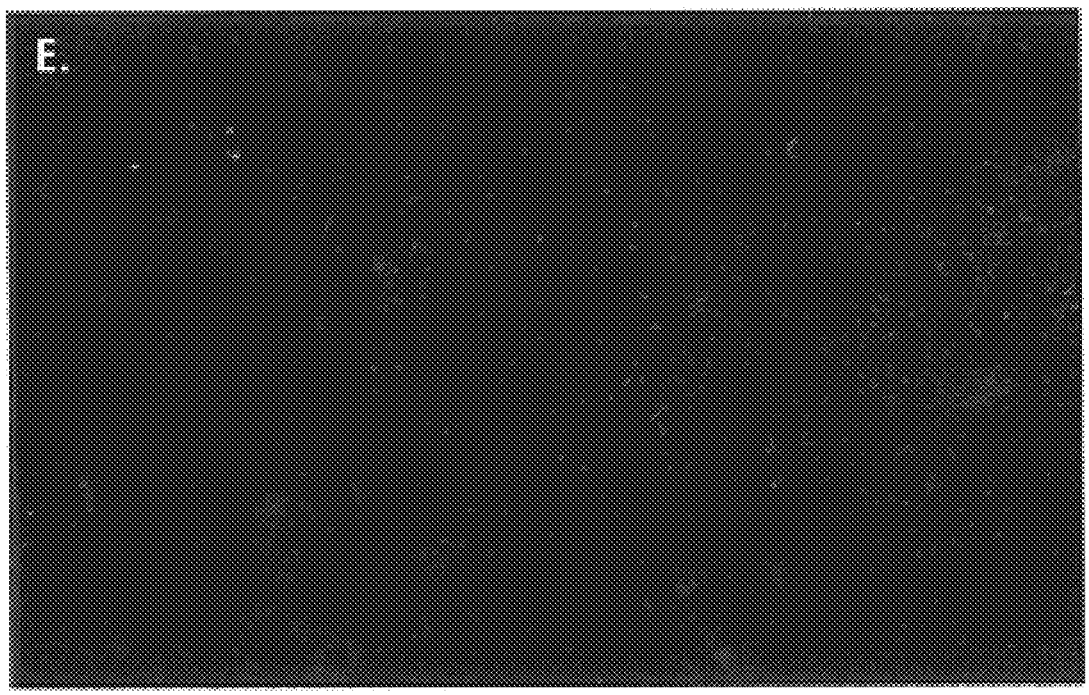

Frozen sections of primary and metastatic melanoma tissue were stained with 18 μg/ml HDC3-14 or HDC318-325 pAb. A strong cytoplasmic staining was observed in primary lesions with both antibodies (FIGS. 2A and B). Both antibodies showed a more uneven distribution of cytoplasmic staining in the metastatic cells compared to cells from primary lesions (FIGS. 2C and D).

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A purified, isolated avian antibody which specifically binds to the native form of human histidine decarboxylase and which specifically binds to EPEEYRERGREM (SEQ ID NO:1) or VKDKYKLQ (SEQ ID NO:2) or a portion of SEQ ID NO:1 or SEQ ID NO:2.

2. The purified antibody of claim 1 which specifically binds to EPEEYRERGREM (SEQ ID NO:1) or a portion of SEQ ID NO:1.

3. The purified antibody of claim 1 which specifically binds to VKDKYKLQ (SEQ ID NO:2) or a portion of SEQ ID NO:2.

4. A preparation of polyclonal antibodies comprising the antibody of claim 1.

5. The purified antibody of claim 4 which comprises IgY.

6. A diagnostic kit for detecting histidine decarboxylase in cells of a mammalian physiological sample which comprises packaging, containing, separately packaged:

(a) a known amount of a first antibody which specifically binds to EPEEYRERGREM (SEQ ID NO:1) or VKDKYKLQ (SEQ ID NO:2); and (b) a known amount of a second antibody, which binds to the first antibody and does not specifically bind to histidine decarboxylase, wherein the second antibody is detectably labeled or binds to a detectable label.

7. A diagnostic kit for detecting melanoma in cells of a mammalian physiological sample which comprises packaging, containing, separately packaged:
(a) a known amount of a first antibody which specifically binds to EPEEYRERGREM (SEQ ID NO:1) or VKDKYKLQ (SEQ ID NO:2); and
(b) a known amount of a second antibody, which binds to the first antibody and does not specifically bind to histidine decarboxylase, wherein the second antibody is detectably labeled or binds to a detectable label.

8. The kit of claim 6 or 7 wherein the first antibody is a preparation of polyclonal antibodies.

9. The kit of claim 6 or 7 wherein the first antibody is a monoclonal antibody.

10. A purified, isolated monoclonal antibody which specifically binds to the native form of human histidine decarboxylase and which specifically binds to EPEEYRGREM (SEQ ID NO:1) or VKDKYKLQ (SEQ ID NO:2) or a portion of SEQ ID NO:1 or SEQ ID NO:2.

11. The purified antibody of claim 10 which specifically binds to EPEEYRERGREM (SEQ ID NO:1) or a portion of SEQ ID NO:1.

12. The purified antibody of claim 10 which specifically binds to VKDKYKLQ (SEQ ID NO:2) or a portion of SEQ ID NO:2.

13. A purified, isolated polyclonal antibody which specifically binds to the native form of human histidine decarboxylase and which specifically binds to EPEEYRERGREM (SEQ ID NO:1) or VKDKYKLQ (SEQ ID NO:2) or a portion of SEQ ID NO:1 or SEQ ID NO:2 and which does not bind to rheumatoid factor.

* * * * *

UNITED STATES PATENT AND TRADEMARK OFFICE
CERTIFICATE OF CORRECTION

PATENT NO. : 6,297,361 B1
DATED : October 2, 2001
INVENTOR(S) : Haak-Frendscho et al.

It is certified that error appears in the above-identified patent and that said Letters Patent is hereby corrected as shown below:

Column 4,
Line 36, delete "presence melanoma" and insert -- presence of melanoma --, therefor.

Column 8,
Line 46, delete "Immunol.ogically" and insert -- Immunologically --, therefor.

Column 10,
Line 43, delete "primer prepared" and insert -- primer is prepared --, therefor.

Column 20,
Line 1, delete "EPEEYRGREM" and insert -- EPEEYRERGREM --, therefor.

Signed and Sealed this

Twenty-first Day of May, 2002

Attest:

JAMES E. ROGAN
Director of the United States Patent and Trademark Office

Attesting Officer

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 12 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Glu Pro Glu Glu Tyr Arg Glu Arg Gly Arg Glu Met
1               5                   10

(2) INFORMATION FOR SEQ ID NO:2:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

Val Lys Asp Lys Tyr Lys Leu Gln
1               5

(2) INFORMATION FOR SEQ ID NO:3:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:3:

AATCTTCAAG CACATGTC                                              18

(2) INFORMATION FOR SEQ ID NO:4:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:4:

CTGGATAGTG GCCGGGATGA　　　　　　　　　　　　　　　　　　　　　　　　　　20

(2) INFORMATION FOR SEQ ID NO:5:

(i) SEQUENCE CHARACTERISTICS:
        (A) LENGTH: 662 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Met Met Glu Pro Glu Glu Tyr Arg Glu Arg Gly Arg Glu Met Val Asp
 1               5                  10                  15

Tyr Ile Cys Gln Tyr Leu Ser Thr Val Arg Glu Arg Val Thr Pro
                20                  25                  30

Asp Val Gln Pro Gly Tyr Leu Arg Ala Gln Leu Pro Glu Ser Ala Pro
                35                  40                  45

Glu Asp Pro Asp Ser Trp Asp Ser Ile Phe Gly Asp Ile Glu Arg Ile
            50                  55                  60

Ile Met Pro Gly Val Val His Trp Gln Ser Pro His Met His Ala Tyr
65                  70                  75                  80

Tyr Pro Ala Leu Thr Ser Trp Pro Ser Leu Leu Gly Asp Met Leu Ala
                85                  90                  95

Asp Ala Ile Asn Cys Leu Gly Phe Thr Trp Ala Ser Ser Pro Ala Cys
                100                 105                 110

Thr Glu Leu Glu Met Asn Val Met Asp Trp Leu Ala Lys Met Leu Gly
            115                 120                 125

Leu Pro Glu His Phe Leu His His Pro Ser Ser Gln Gly Gly Gly
            130                 135                 140

Val Leu Gln Ser Thr Val Ser Glu Ser Thr Leu Ile Ala Leu Leu Ala
145                 150                 155                 160

Ala Arg Lys Asn Lys Ile Leu Glu Met Lys Thr Ser Glu Pro Asp Ala
                165                 170                 175

Asp Glu Ser Cys Leu Asn Ala Arg Leu Val Ala Tyr Ala Ser Asp Gln
                180                 185                 190

Ala His Ser Ser Val Glu Lys Ala Gly Leu Ile Ser Leu Val Lys Met
            195                 200                 205

Lys Phe Leu Pro Val Asp Asp Asn Phe Ser Leu Arg Gly Glu Ala Leu
210                 215                 220

Gln Lys Ala Ile Glu Glu Asp Lys Gln Arg Gly Leu Val Pro Val Phe
225                 230                 235                 240

Val Cys Ala Thr Leu Gly Thr Thr Gly Val Cys Ala Phe Asp Cys Leu
                245                 250                 255

Ser Glu Leu Gly Pro Ile Cys Ala Arg Glu Gly Leu Trp Leu His Ile
            260                 265                 270

Asp Ala Ala Tyr Ala Gly Thr Ala Phe Leu Cys Pro Glu Phe Arg Gly
            275                 280                 285

Phe Leu Lys Gly Ile Glu Tyr Ala Asp Ser Phe Thr Phe Asn Pro Ser
290                 295                 300

Lys Trp Met Met Val His Phe Asp Cys Thr Gly Phe Trp Val Lys Asp
305                 310                 315                 320

Lys Tyr Lys Leu Gln Gln Thr Phe Ser Val Asn Pro Ile Tyr Leu Arg
                325                 330                 335
```

```
His Ala Asn Ser Gly Val Ala Thr Asp Phe Met His Trp Gln Ile Pro
            340             345             350
Leu Ser Arg Arg Phe Arg Ser Val Lys Leu Trp Phe Val Ile Arg Ser
            355             360             365
Phe Gly Val Lys Asn Leu Gln Ala His Val Arg His Gly Thr Glu Met
            370             375             380
Ala Lys Tyr Phe Glu Ser Leu Val Arg Asn Asp Pro Ser Phe Glu Ile
385                 390             395                 400
Pro Ala Lys Arg His Leu Gly Leu Val Val Phe Arg Leu Lys Gly Pro
                405             410             415
Asn Cys Leu Thr Glu Asn Val Leu Lys Glu Ile Ala Lys Ala Gly Arg
                420             425             430
Leu Phe Leu Ile Pro Ala Thr Ile Gln Asp Lys Leu Ile Ile Arg Phe
            435             440             445
Thr Val Thr Ser Gln Phe Thr Thr Arg Asp Asp Ile Leu Arg Asp Trp
            450             455             460
Asn Leu Ile Arg Asp Ala Ala Thr Leu Ile Leu Ser Gln His Cys Thr
465             470             475             480
Ser Gln Pro Ser Pro Arg Val Gly Asn Leu Ile Ser Gln Ile Arg Gly
                485             490             495
Ala Arg Ala Trp Ala Cys Gly Thr Ser Leu Gln Ser Val Ser Gly Ala
                500             505             510
Gly Asp Asp Pro Val Gln Ala Arg Lys Ile Ile Lys Gln Pro Gln Arg
            515             520             525
Val Gly Ala Gly Pro Met Lys Arg Glu Asn Gly Leu His Leu Glu Thr
            530             535             540
Leu Leu Asp Pro Val Asp Asp Cys Phe Ser Glu Glu Ala Pro Asp Ala
545             550             555             560
Thr Lys His Lys Leu Ser Ser Phe Leu Phe Ser Tyr Leu Ser Val Gln
                565             570             575
Thr Lys Lys Lys Thr Val Arg Ser Leu Ser Cys Asn Ser Val Pro Val
                580             585             590
Ser Ala Gln Lys Pro Leu Pro Thr Glu Ala Ser Val Lys Asn Gly Gly
            595             600             605
Ser Ser Arg Val Arg Ile Phe Ser Arg Phe Pro Glu Asp Met Met Met
            610             615             620
Leu Lys Lys Ser Ala Phe Lys Lys Leu Ile Lys Phe Tyr Ser Val Pro
625                 630             635                 640
Ser Phe Pro Glu Cys Ser Ser Gln Cys Gly Leu Gln Leu Pro Cys Cys
                645             650             655
Pro Leu Gln Ala Met Val
            660
```